United States Patent [19]

Thum et al.

[11] 4,366,249

[45] Dec. 28, 1982

[54] STORAGE STABLE CHOLESTEROL OXIDASE COMPOSITIONS

[75] Inventors: Waldemar Thum; Gunter Lang; Hellmuth Vetter; Gotthilf Näher, all of Tutzing, Fed. Rep. of Germany

[73] Assignee: Boehringer Mannheim GmbH, Mannheim-Waldhof, Fed. Rep. of Germany

[21] Appl. No.: 339,760

[22] Filed: Jan. 15, 1982

Related U.S. Application Data

[63] Continuation of Ser. No. 903,316, May 5, 1978, abandoned.

[30] Foreign Application Priority Data

Dec. 14, 1977 [DE] Fed. Rep. of Germany ....... 2755799

[51] Int. Cl.$^3$ .......................... C12N 9/96; C12N 9/04
[52] U.S. Cl. ..................................... 435/188; 435/190
[58] Field of Search ............................... 435/188, 190

[56] References Cited

FOREIGN PATENT DOCUMENTS 52-143285 11/1977 Japan .

OTHER PUBLICATIONS

Theorell et al., Acta Chemica Scandinavia vol. 3, pp. 1649–1658 (1954).
Yoshida et al., Chemical Abstracts vol. 88, 134873n (1978) (Abstract of Japan Kokai 77,143,285).

Primary Examiner—Lionel M. Shapiro
Attorney, Agent, or Firm—Felfe & Lynch

[57] ABSTRACT

Storage-stable aqueous cholesterol oxidase compositions comprising cholestrol oxidase, a buffer and from 2 to 3.5 M sodium or potassium chloride as a stabilizing agent, are significantly superior to conventional compositions with respect to storage stability and fungibility.

5 Claims, No Drawings

STORAGE STABLE CHOLESTEROL OXIDASE COMPOSITIONS

This is a continuation of application Ser. No. 903,316 filed May 5, 1978 now abandoned.

The invention relates to a storable aqueous cholesterol oxidase preparation containing buffer and stabilizing agent.

The enzymatic activity of a protein is determined by the spatial arrangement of the amino acid radical in its polypeptide chains. This "conformation" is affected in aqueous solution by the presence of electrically charged or uncharged inorganic as well as organic molecules. Consequently, enzymes in aqueous solution are very delicate and are highly susceptible to a loss in activity. Aqueous enzyme preparations, therefore, have to be stabilized.

It is known that the anionic as well as cationic components of inorganic salts of low molecular weight, can have either a stabilizing or a denaturing influence on the conformation of the enzyme. Such anions and cations are classified with regard to this action in what is known as the Hoffmeister Series ("Structure and Stability of Biological Macromolecules," by Timasheff and Fasman, publisher Mercel Dekker, Inc., New York, 1969, page 427). In the Hoffmeister Series; anions and cations act, each independently of the other, either in a more stabilizing or more denaturing manner. The list of those having stabilizing action is headed by the sulfate anion and quaternary ammonium ions, followed by the ammonium ion. It is therefore easy to understand why most of the commercial enzyme preparations contain ammonium sulfate as stabilizer, alone, or in some cases together with additional specific stabilizers. Cholesterol oxidase has hitherto been stabilized in commercial aqueous solution with ammonium sulfate.

However, it has been found that the stability of cholesterol oxidase in ammonium sulfate solution is not satisfactory. The best stabilizing action has been achieved at approximately 1 M ammonium sulfate, and diminishes at higher ammonium sulfate concentration.

Even at a concentration of 1 M, however, coarsely floccular fatty precipitation of the enzyme occasionally occurs; these precipitates are still enzymatically active, but they interfere with dosing during packing operations.

Surprisingly, it has now been found that this difficulty can be eliminated and, on the one hand, precipitation can be entirely prevented, while on the other hand, a superior stabilization is achieved if sodium chloride or potassium chloride is used as stabilizing agent in a concentration between 2.0 M and 3.5 M.

The invention thus relates to a storable aqueous cholesterol oxidase preparation having a content of buffer and stabilizing agent, which is characterized in that it contains 2 to 3.5 M of sodium chloride or potassium chloride as stabilizing agent. Preferably, it contains sodium chloride in a concentration between 2.5 and 3.2 M.

The superior stabilizing action of the above-named salts was not to have been expected, because in the Hoffmeister Series, potassium and sodium are less stabilizing, i.e., more inactivating, than ammonium, and also chloride inactivates considerably more than does sulfate. Furthermore, it is known that flavine enzymes, which include cholesterol oxidase, are inactivated by alkali chlorides at higher concentration (Theorell, in Acta Chem. Scand. 3, 1954, p. 1649).

Under the conditions described above, there is good stability at pH values between 4.5 and 8.5. Preferably, the cholesterol oxidase preparation of the invention has a pH between 5.0 and 6.5. The buffer molarity ranges generally between 0.01 M and 0.2 M, the range from 0.01 M to 0.1 M being preferred.

All salts which buffer in the above-stated range can be used as buffer substances, examples being potassium phosphate buffer, sodium phosphate buffer, potassium phosphatecitric acid buffer, sodium acetate buffer, etc.

In a number of cases in the past, enzymes have been stored in alkali chloride solutions. This was done, however, for different reasons, as for example the ease of crystallizing papain in sodium chloride in comparison with ammonium chloride, or the purification of lectins by chromatography in sodium chloride solutions, so that poorer stability was acceptable. However, such a method of storage was unknown in the case of flavine enzymes since it results in the cleavage of the prosthetic group at acid pH values.

The superior storability of the cholesterol oxidase preparations of the invention in comparison with cholesterol oxidase preparations stabilized with ammonium sulfate will appear from the following experiments.

A batch of cholesterol oxidase having a content of 450 units of enzyme per milliliter in 0.05 M potassium phosphate buffer, pH 6, was adjusted to the salt concentration listed in the following table and maintained for 4 weeks at 4° C. and at +35° C. The residual activity found at the end of this period is shown in the following table (two-week values between parentheses).

TABLE I

| Test Temperature | Kind of additive and concentration | | |
|---|---|---|---|
| | 1 M AS | 3 M NaCl | 3 M KCl |
| +4° C. | (100%) 100% turbid | (96%) 96% clear | (100%) 100% clear |
| +33° C. | (86%) 55% turbid | (88%) 88% clear | (91%) 87% clear |

The superior stabilization in accordance with the invention is obtained independently of the enzyme concentration and of the enzyme batch (individual batches often differ in their stability), and it is even more pronounced if it is compared, not with molar ammonium sulfate, but with molar ammonium sulfate solution.

Two different enzyme batches were adjusted to a concentration of 300 U/ml and 30 U/ml, with the above-specified buffer, and then stored for 4 weeks at 35° C. as described above. The following table gives the residual activities measured 4 weeks later. The two-week values are given in parentheses.

TABLE II

| Batch | Enzyme Concentration | 1 M AS | 3 M As | 3 M NaCl |
|---|---|---|---|---|
| 1 | 300 U/ml | (73%) 58% | | (100%) 92% |
| | 30 U/ml | (77%) 57% | (68%) 49% | (100%) 96% |
| 2 | 300 U/ml | (73%) 68% | | (100%) 88% |
| | 30 U/ml | (55%) 55% | (87%) 33% | (100%) 88% |

To show that the superior stabilization in accordance with the invention is limited to a certain concentration range, the above-described storage test was performed on an enzyme batch of a concentration of 30 U/ml at 4° C. and at 35° C. for four weeks (2 weeks) with two different ammonium sulfate and four different sodium chloride

TABLE III

| Temp. | Ammonium sulfate | | | Sodium Chloride | | |
| --- | --- | --- | --- | --- | --- | --- |
| | 1 M | 3.2 M | 2 M | 3 M | 4 M | 5 M |
| +4° C. | (95%) | (100%) | (72%) | (64%) | (76%) | (100%) |
| | 100% | 90% | 95% | 95% | 80% | 80% |
| +35° C. | (72%) | (61%) | (88%) | (88%) | (26%) | (16%) |
| | 46% | 45% | 71% | 77% | 40% | 0 |

It will be understood that the specification and examples are illustrative but not limitative of the present invention and that other embodiments within the spirit and scope of the invention will suggest themselves to those skilled in the art.

What is claimed is:

1. Storable aqueous cholesterol oxidase compositions comprising cholesterol oxidase, a buffer and from 2 to 3.5 M of sodium chloride or potassium chloride as a stabilizing agent.

2. Composition as claimed in claim 1, containing 2.5 to 3.2 M of sodium chloride.

3. Composition as claimed in claim 1, having a pH of between 4.5 and 8.5.

4. Composition as claimed in claim 3, having a pH of between 5 and 6.5.

5. Composition as claimed in claim 1, containing a buffer comprising a buffer salt in a concentration of 0.01 to 0.5 M.

* * * * *